US009655647B2

(12) United States Patent
McKinnis et al.

(10) Patent No.: US 9,655,647 B2
(45) Date of Patent: May 23, 2017

(54) APPARATUS AND METHOD FOR THE RETRIEVAL OF AN INTRAVASCULAR FILTER

(71) Applicant: Muffin Incorporated, West Lafayette, IN (US)

(72) Inventors: Peter S. McKinnis, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 10 days.

(21) Appl. No.: 14/086,219

(22) Filed: Nov. 21, 2013

(65) Prior Publication Data
US 2014/0172008 A1 Jun. 19, 2014

Related U.S. Application Data

(60) Provisional application No. 61/739,088, filed on Dec. 19, 2012.

(51) Int. Cl.
  *A61B 17/50* (2006.01)
  *A61F 2/01* (2006.01)

(52) U.S. Cl.
  CPC .............. *A61B 17/50* (2013.01); *A61F 2/01* (2013.01); *A61F 2002/011* (2013.01);
  (Continued)

(58) Field of Classification Search
  CPC  A61F 2002/011; A61F 2/01; A61F 2002/016; A61F 2002/018;
  (Continued)

(56) References Cited

U.S. PATENT DOCUMENTS 3,672,367 A   6/1972  Scislowicz
4,525,157 A   6/1985  Vaillancourt
(Continued)

FOREIGN PATENT DOCUMENTS

WO   WO 2007/079410 A2   7/2007
WO   WO 2012/003369 A2   1/2012

OTHER PUBLICATIONS

International Search Report and Written Opinion issued in PCT/US2013/071254, dated Mar. 10, 2014.
European Search Report Jun. 9, 2016 from EP13864888.

*Primary Examiner* — Robert Lynch
*Assistant Examiner* — Socrates L Boutsikaris
(74) *Attorney, Agent, or Firm* — Woodard Emhardt Moriarty McNett & Henry LLP

(57) ABSTRACT

A retrieval apparatus for removing an intravascular filter from a body vessel of a patient includes an outer sheath defining an outer lumen, an inner sheath defining an inner lumen wherein the inner sheath is positioned within the outer lumen, a retrieval member positioned in the inner lumen, an ultrasound transducer positioned on the application side of the retrieval member, a guide wire cannula extending between the outer sheath and the inner sheath, the guide wire cannula including an application side end, and a dilator located at an application side end of the retrieval apparatus, said dilator being coupled to said ultrasound transducer and receiving the application side end of said guide wire cannula.

28 Claims, 8 Drawing Sheets

(52) U.S. Cl.
CPC ... *A61F 2002/016* (2013.01); *A61F 2230/005* (2013.01); *A61F 2230/0067* (2013.01); *A61F 2250/0093* (2013.01)

(58) Field of Classification Search
CPC ...... A61F 2230/0067; A61F 2230/0006; A61F 2230/008; A61F 2230/005; A61F 2/013; A61B 17/50; A61B 17/221; A61B 17/32056; A61B 2017/22035; A61B 2017/2212; A61B 2017/2215; A61B 2017/00358; A61B 8/445; A61B 8/4461; A61B 8/0841; A61B 8/4245; A61B 2090/3925; A61B 2090/378; A61B 1/018; A61B 1/05; A61B 6/12; A61B 90/36
USPC ......................................................... 606/200
See application file for complete search history.

(56) References Cited

U.S. PATENT DOCUMENTS

| | | | |
|---|---|---|---|
| 5,325,860 A * | 7/1994 | Seward | A61B 8/06 600/439 |
| 5,415,630 A | 5/1995 | Gory et al. | |
| 5,545,151 A * | 8/1996 | O'Connor et al. | 604/524 |
| 6,120,494 A | 9/2000 | Jonkman | |
| 6,306,097 B1 * | 10/2001 | Park | A61B 1/00154 600/466 |
| 6,342,062 B1 * | 1/2002 | Suon et al. | 606/200 |
| 6,440,077 B1 | 8/2002 | Jung et al. | |
| 6,458,145 B1 * | 10/2002 | Ravenscroft et al. | 606/200 |
| 6,554,801 B1 * | 4/2003 | Steward | A61B 8/12 600/464 |
| 6,645,152 B1 | 11/2003 | Jung et al. | |
| 7,011,681 B2 * | 3/2006 | Vesely | 623/2.11 |
| 7,591,813 B2 | 9/2009 | Levine et al. | |
| 7,625,390 B2 | 12/2009 | Hendriksen et al. | |
| 7,699,867 B2 | 4/2010 | Hendriksen et al. | |
| 7,717,865 B2 | 5/2010 | Boutillette et al. | |
| 7,803,171 B1 | 9/2010 | Uflacker | |
| 8,043,324 B2 | 10/2011 | Deshpande et al. | |
| 2006/0069405 A1 | 3/2006 | Schaeffer et al. | |
| 2006/0184193 A1 | 8/2006 | Lowe et al. | |
| 2008/0103456 A1 | 5/2008 | Johnson et al. | |
| 2008/0119867 A1 | 5/2008 | Delaney | |
| 2009/0118760 A1 | 5/2009 | Clausen et al. | |
| 2009/0182370 A1 | 7/2009 | Volobuyev et al. | |
| 2009/0248142 A1 * | 10/2009 | Perkins | A61F 2/95 623/1.24 |
| 2009/0326560 A1 | 12/2009 | Lampropoulos et al. | |
| 2011/0295306 A1 | 12/2011 | Blatter | |
| 2012/0022578 A1 | 1/2012 | Jantzen et al. | |
| 2012/0041473 A1 | 2/2012 | Nigon | |
| 2012/0239130 A1 * | 9/2012 | Hartley | A61F 2/95 623/1.12 |
| 2013/0184738 A1 * | 7/2013 | Laroya | A61B 17/221 606/200 |

\* cited by examiner

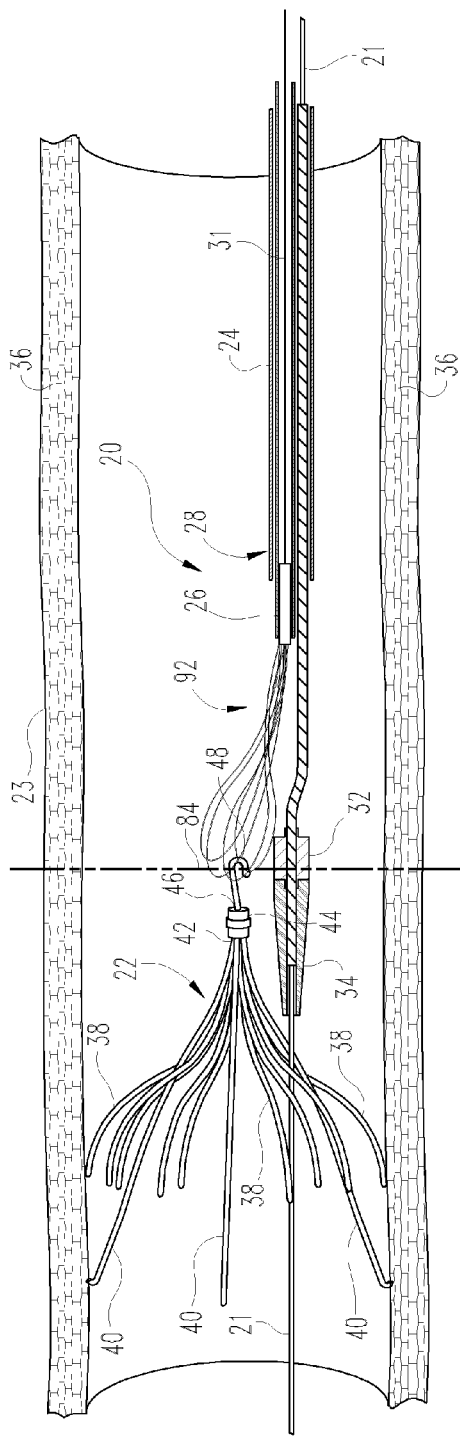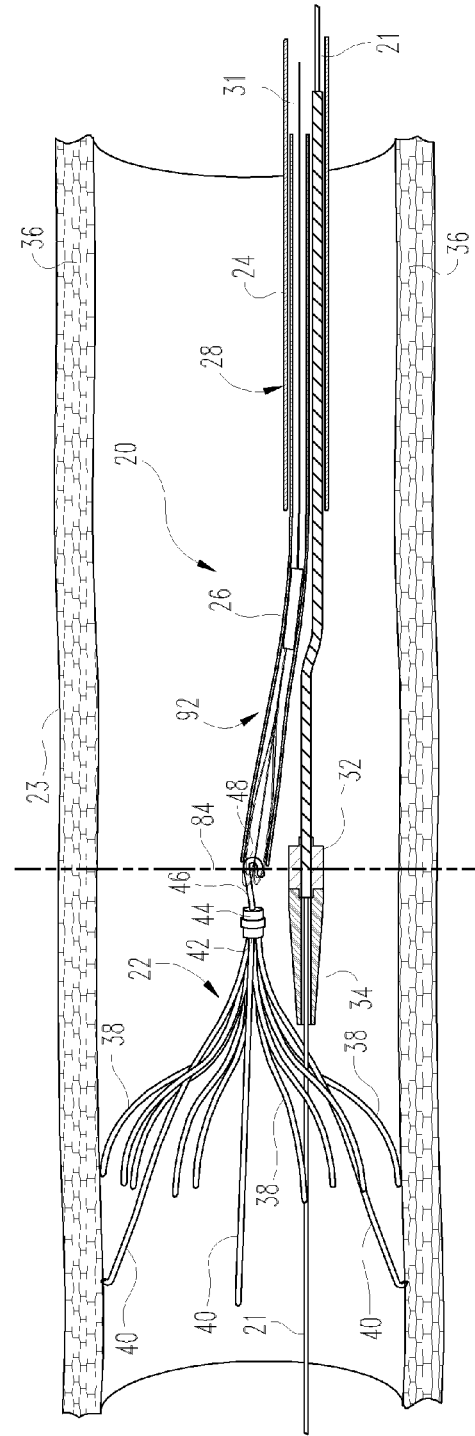

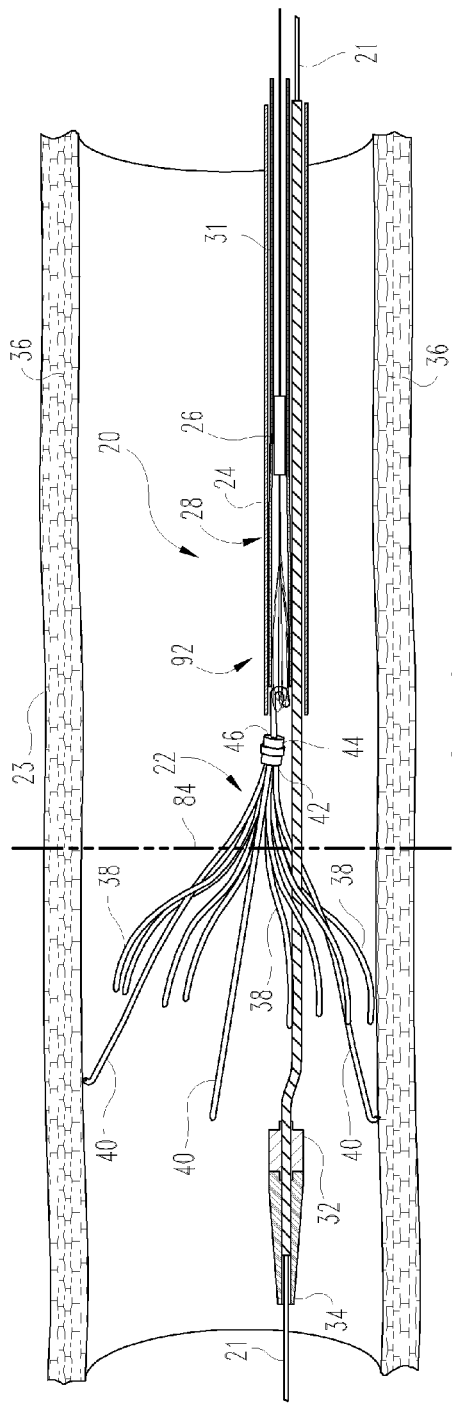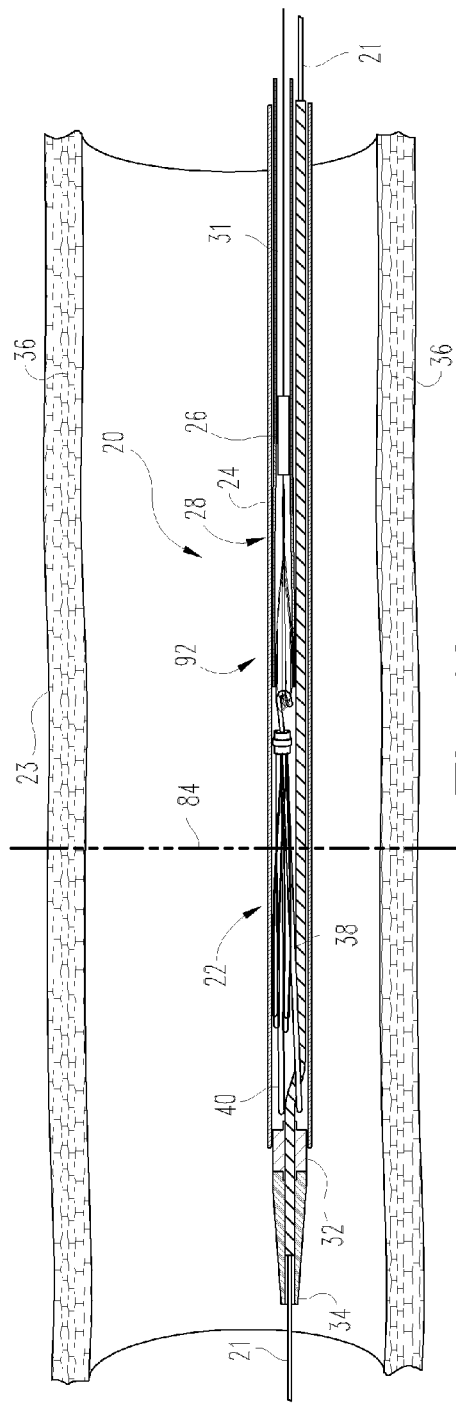

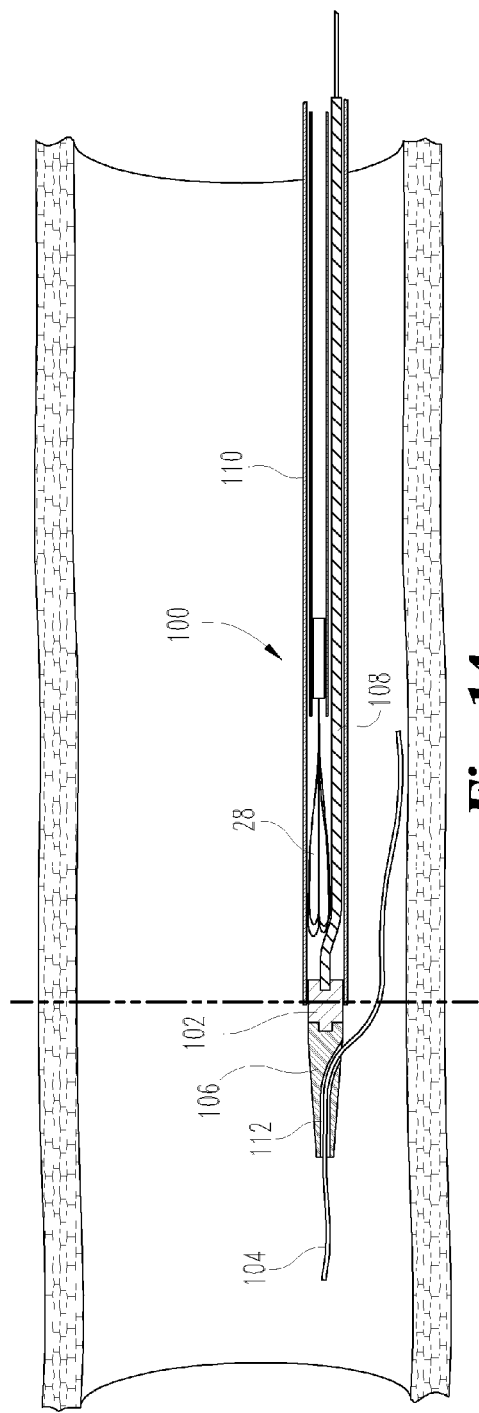
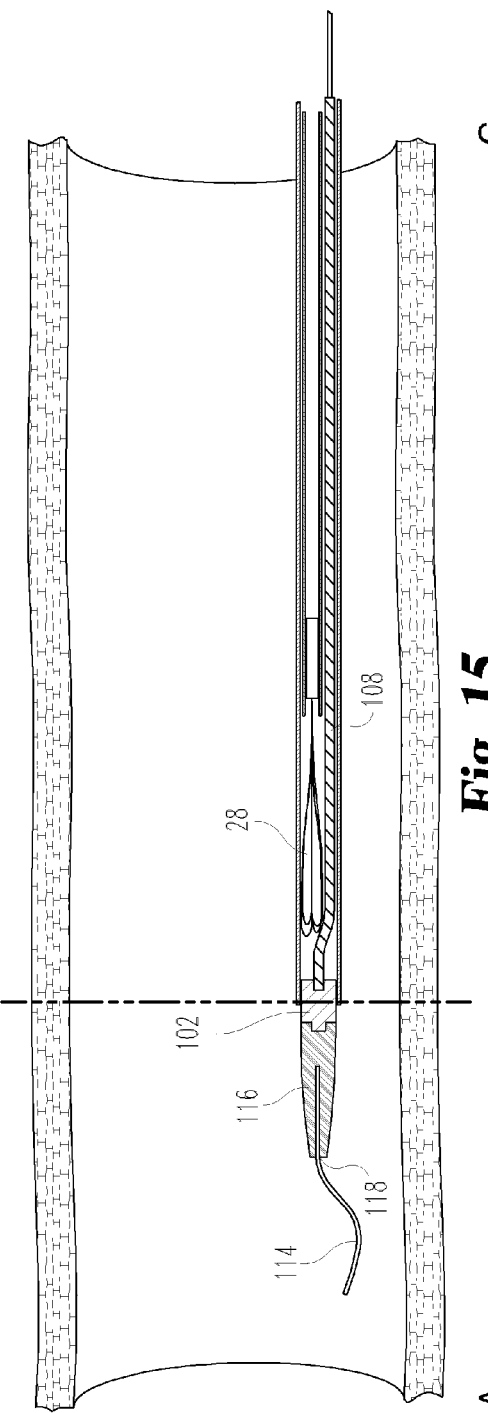

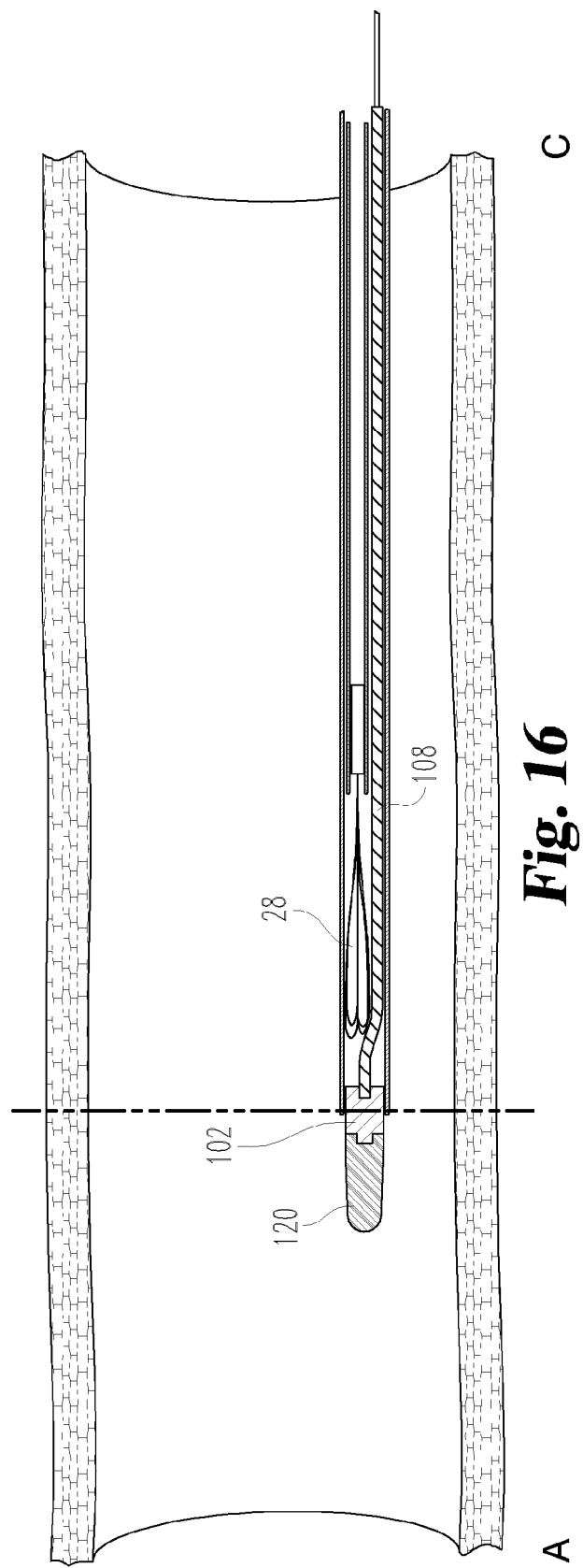

APPARATUS AND METHOD FOR THE RETRIEVAL OF AN INTRAVASCULAR FILTER

CROSS REFERENCE TO RELATED APPLICATION

This application claims the benefit of U.S. Provisional Application No. 61/739,088 filed Dec. 19, 2012, which is hereby incorporated by reference.

BACKGROUND

Disclosed is an apparatus for use in the retrieval of an intravascular filter which has previously been emplaced in a blood vessel. Also disclosed is a method for using the disclosed apparatus in the retrieval of an intravascular filter.

A need for an intravascular filtering device can arise, for example, in trauma patients, orthopedic surgery patients, neurosurgery patients, or in patients having medical conditions requiring bed rest or non-movement. During such medical conditions, the need for filtering devices arises when there is a likelihood of thrombosis in the peripheral vasculature of patients wherein clot material, stenosis material or other particles break away from the vessel wall, risking downstream blockage of the vessel or other damage. For example, depending on the size, such break-away material could post a serious risk of pulmonary embolism, i.e. wherein blood clots migrate from the peripheral vasculature through the heart and into the lungs. A filtering device can be deployed in a vasculature of a patient when, for example, anticoagulant therapy is contraindicated or has failed. In more recent years, filters have been used or considered in preoperative patients and in patients predisposed to thrombosis which places the patient at risk for embolism.

The design focus of an intravascular filter of the type described, such as an IVC filter, is on providing a structure which is capable of trapping these emboli so as to prevent them from reaching the heart and lungs. The specific focus of the disclosed apparatus and method, as exemplified by the illustrated and described embodiments, is directed to retrieval of an intravascular filter which has been emplaced in the inferior vena cava (IVC) and then removal of that intravascular filter from the patient. The IVC represents a preferred placement location in the patient in order to address concerns over emboli which may originate in the veins of the leg or pelvis, i.e. deep vein thrombosis (DVT). For such emboli the flow path to the heart and lungs includes passage through the IVC. As used herein, the term "emboli" refers to something which travels through the bloodstream and which has a structural configuration such that it could become lodged in a blood vessel and create some degree of blockage to flow through the blood vessel.

The benefits of an intravascular filter have been well established. However, in many cases such filters have not been considered removable from a patient due to the likelihood of endotheliosis of the filter or fibrous reaction matter adherent to the endothelium during treatment. Following deployment of an intravascular filter in a patient, proliferating intimal cells can begin to accumulate around the filter struts which contact the wall of the vessel. After a length of time, such ingrowth may prevent removal of the filter, or may risk significant trauma during removal through a layer of endothelium, requiring the filter to remain in the patient.

The focus of this disclosure is on the method of retrieval and removal of an intravascular filter which has been emplaced in a patient, including the method or means of guidance of the retrieval apparatus throughout the various steps of the retrieval and removal process.

In order to help "visualize" the placement, positioning and orientation of an emplaced IVC filter for purposes of retrieval and ultimately removal, the currently performed procedure uses fluoroscopic guidance. This procedure uses a percutaneous retrieval set and fluoroscopy suite. Further, transport of the patient to the fluoroscopy suite is required and this can be difficult and time consuming, especially for trauma patients. While a removal hook is a structural part of the IVC filter construction which is described herein, that removal hook still must be located in some fashion and the orientation of that hook must be visualized when it is going to be used as part of the retrieval procedure.

The retrieval procedure according to the present disclosure uses an intravascular ultrasound (IVUS) transducer for visual guidance of the retrieval apparatus, the IVC filter and the steps associated with the overall retrieval and removal procedure. Included as part of the retrieval apparatus is a snare which is designed so that it can be easily seen and located under IVUS guidance. By incorporating the IVUS transducer into the retrieval apparatus, including the use of a dilator, the retrieval procedure can be performed through a single access point. Performance of a retrieval procedure under ultrasound guidance is not possible using currently approved (prior art) technology. The imaging and visualization provided by the exemplary embodiment affords the clinician a higher confidence level in the procedure and results in a safe procedure.

SUMMARY

A retrieval apparatus for removing an intravascular filter from a body vessel of a patient includes an outer sheath defining an outer lumen, an inner sheath defining an inner lumen wherein the inner sheath is positioned within the outer lumen, a retrieval member positioned in the inner lumen, an ultrasound transducer positioned to the application side of the retrieval member, a guide wire cannula extending between the outer sheath and the inner sheath, the guide wire cannula including an application side end, and a dilator located at an application side end of the retrieval apparatus, said dilator being coupled to said ultrasound transducer and receiving the application side end of said guide wire cannula.

A retrieval apparatus for retrieval of an IVC filter from the IVC of a patient includes an outer sheath defining an outer lumen, an inner sheath defining an inner lumen, a retrieval member positioned in the inner lumen, an IVUS transducer positioned to the application side of the retrieval member, a guide wire cannula extending between the outer sheath and the inner sheath, the guide wire cannula including an application side end and a dilator located at an application side end of the retrieval apparatus, said dilator being coupled to an application side portion of the IVUS transducer.

A method of retrieving an intravascular filter from a body vessel of a patient using a retrieval apparatus which includes an outer sheath, an inner sheath, a retrieval member, an ultrasound transducer, a guide wire cannula and a dilator wherein the method includes the steps of providing the retrieval apparatus, inserting the retrieval apparatus into the body vessel, positioning the retrieval apparatus at a selected location, manipulating the retrieval apparatus so as to move a portion of the retrieval member, closing the retrieval member on a portion of the intravascular filter and withdrawing the retrieval apparatus with the intravascular filter.

BRIEF DESCRIPTION OF THE DRAWINGS

FIG. 10 is a diagrammatic illustration of another one of the retrieval steps associated with the use of the FIG. 1 retrieval apparatus.

FIG. 11 is a diagrammatic illustration of another one of the retrieval steps associated with the use of the FIG. 1 retrieval apparatus.

FIG. 12 is a diagrammatic illustration of another one of the retrieval steps associated with the use of the FIG. 1 retrieval apparatus.

FIG. 13 is a diagrammatic illustration of another one of the retrieval steps associated with the use of the FIG. 1 retrieval apparatus.

FIG. 14 is a partial, diagrammatic, side elevational view of an alternative transducer tip and wire guide arrangement according to the present disclosure.

FIG. 15 is a partial, diagrammatic, side elevational view of an alternative transducer tip and wire guide arrangement according to the present disclosure.

FIG. 16 is a partial, diagrammatic, side elevational view of an alternative transducer tip arrangement according to the present disclosure.

DESCRIPTION OF THE SELECTED EMBODIMENTS

Figure 1:
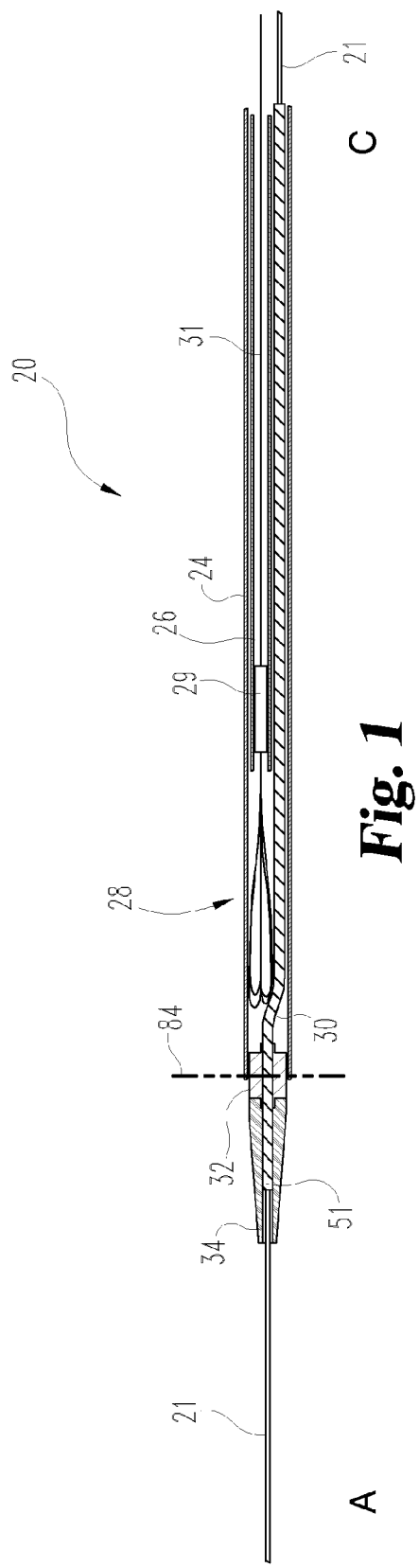
FIG. 1 is a diagrammatic, side elevational view, in partial section, of a retrieval apparatus for an intravascular filter according to the present disclosure.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 2:
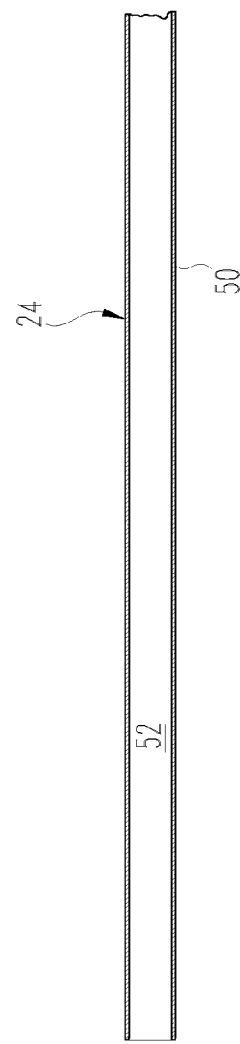
FIG. 2 is a side elevational view, in full section, of an outer sheath which comprises one of the components of the FIG. 1 retrieval apparatus.
Figure 2A:
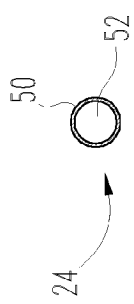
FIG. 2A is an end elevational view, in full form, of the FIG. 2 outer sheath.
Figure 3:
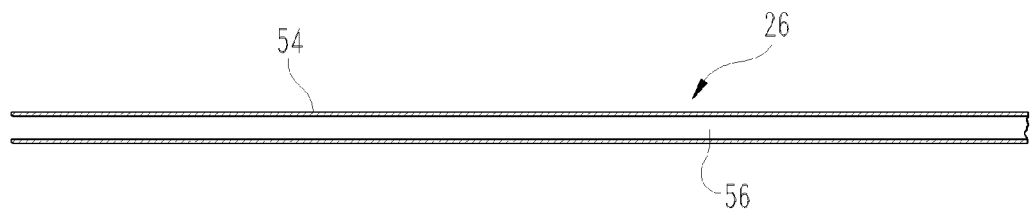
FIG. 3 is a side elevational view, in full section, of an inner sheath which comprises one of the components of the FIG. 1 retrieval apparatus.
Figure 3A:
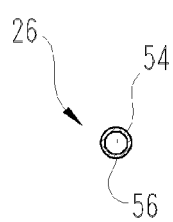
FIG. 3A is an end elevational view, in full form, of the FIG. 3 inner sheath.
Figure 4:
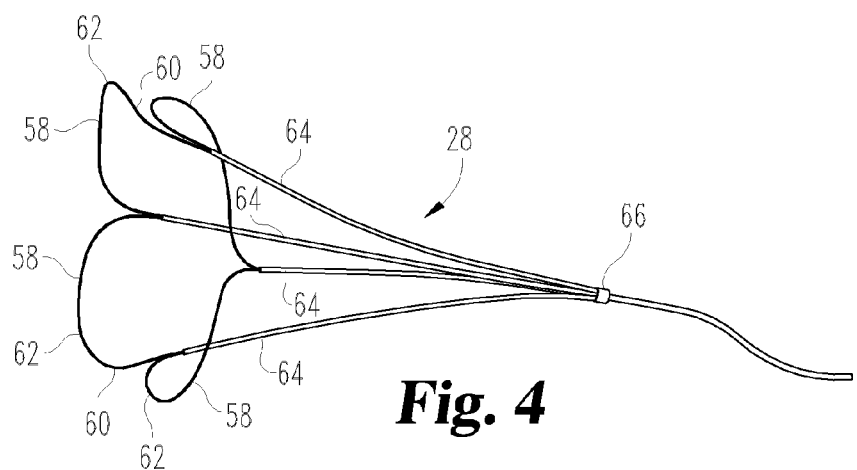
FIG. 4 is a diagrammatic, perspective view of a snare which comprises one of the components of the FIG. 1 retrieval apparatus.
Figure 5:
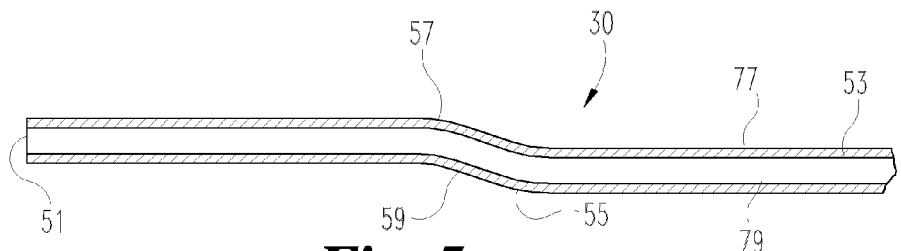
FIG. 5 is a side elevational view, in full section, of a guide wire cannula which comprises one of the components of the FIG. 1 retrieval apparatus.
Figure 5A:
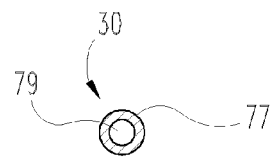
FIG. 5A is an end elevational view, in full form, of the FIG. 5 guide wire cannula.
Figure 6:
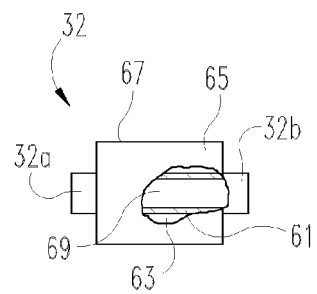
FIG. 6 is a fragmentary, side elevational view of an ultrasound transducer which comprises one of the components of the FIG. 1 retrieval apparatus.
Figure 6A:
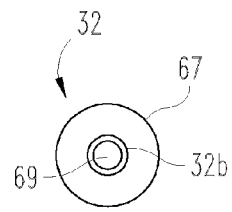
FIG. 6A is an end elevational view of the FIG. 6 ultrasound transducer.
Figure 7:
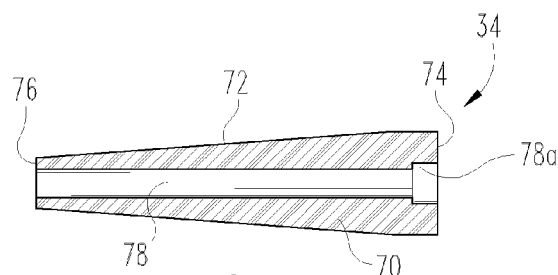
FIG. 7 is a side elevational view, in full section, of a dilator which comprises one of the components of the FIG. 1 retrieval apparatus.
Figure 7A:
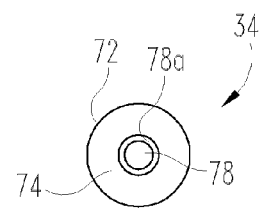
FIG. 7A is a end elevational view, in full form, of the FIG. 7 dilator.
Figure 8:
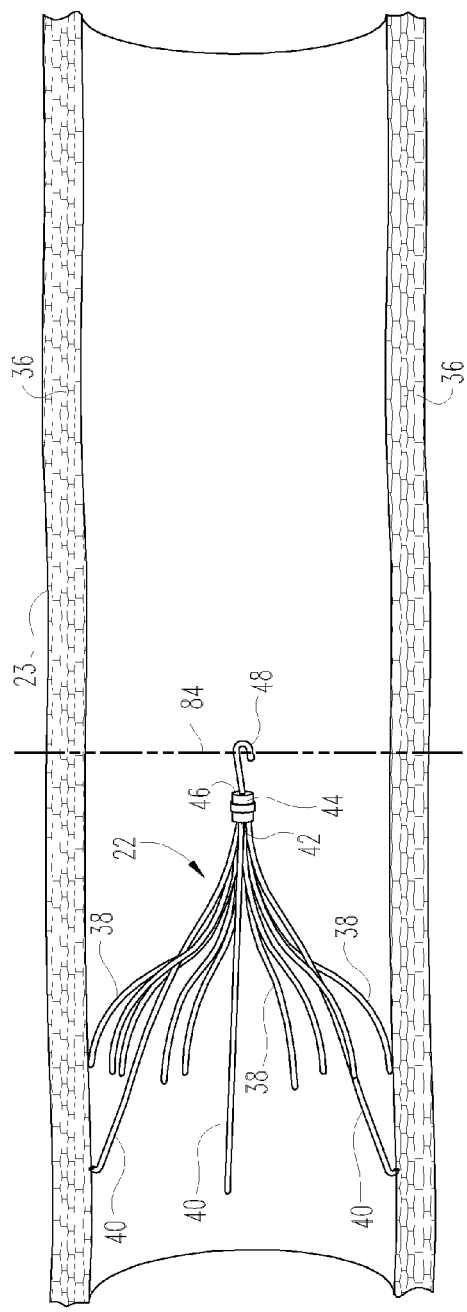
FIG. 8 is a diagrammatic, perspective view of an intravascular filter which has been emplaced in the IVC prior to the use of the FIG. 1 retrieval apparatus.
Figure 9:
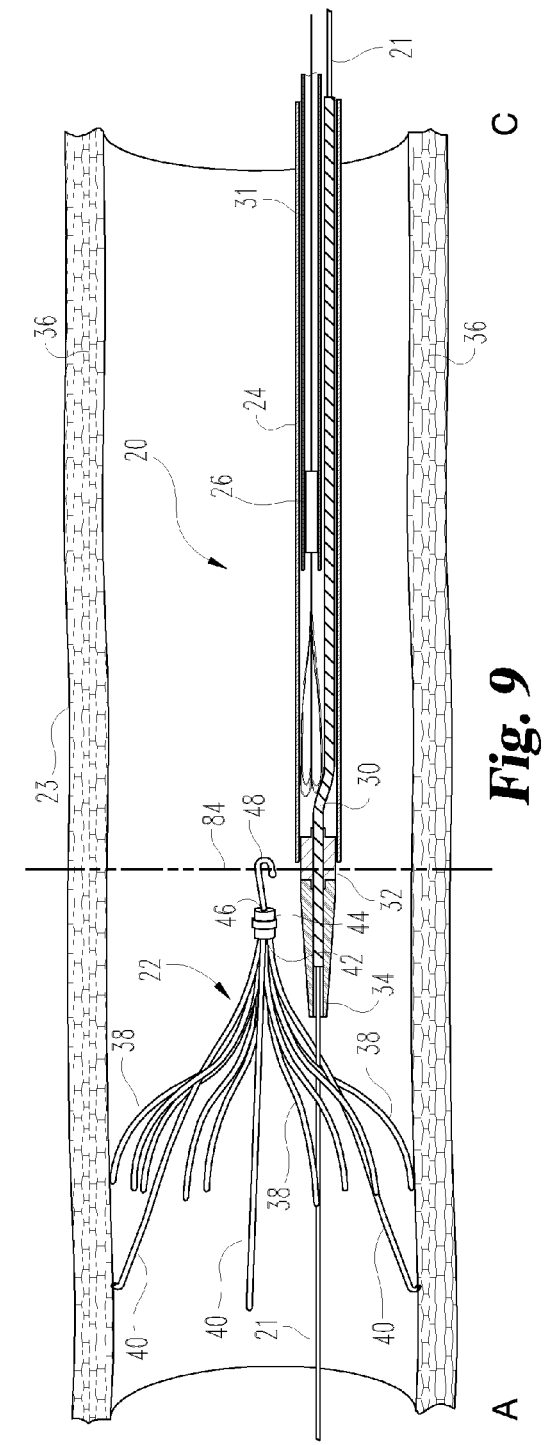
FIG. 9 is a diagrammatic, side elevational view which is a combination of FIGS. 1 and 8 and corresponds to the first step of the retrieval method which is disclosed.

Referring to FIGS. 1, 8 and 9 there is illustrated a retrieval apparatus 20 for an emplaced intravascular filter 22. In the exemplary embodiment intravascular filter 22 is an IVC filter as defined by its positioning the inferior vena cava (IVC) 23. Retrieval apparatus 20 includes an outer sheath 24, an inner sheath 26, a snare 28, a guide wire cannula 30, an ultrasound transducer 32 and a tip which in the exemplary embodiment is dilator 34. The structural details of outer sheath 24 are illustrated in FIGS. 2 and 2A. The structural details of inner sheath 26 are illustrated in FIGS. 3 and 3A. The structural details of snare 28 are illustrated in FIG. 4. The structural details of guide wire cannula 30 are illustrated in FIGS. 5 and 5A. The structural details of ultrasound transducer 32 are illustrated in FIGS. 6 and 6A. The structural details of dilator 34 are illustrated in FIGS. 7 and 7A. Since apparatus 20 is an intravascular apparatus, its size, shape and material selections are all consistent with apparata and devices which need to be emplaced and move within a vein. A section of the IVC 23 (represented by wall 36) is illustrated in FIGS. 8 and 9 for assisting with an understanding of the orientation and the relative positioning of retrieval apparatus 20 and IVC filter 22. One of the important considerations in the manner or method of use of retrieval apparatus 20 is the manner of guiding the retrieval apparatus into position, securing and engagement with the IVC filter 22 and removal of the IVC filter 22. Snare 28 includes a plurality of wire loops 58 integrally joined by way of supporting cannulae 64 with a common securement base. The wires which create the plurality of loops 58 slide through the cannulae 64, with two (2) wire strands per cannula. Also included as part of snare 28 is snare delivery device 29 and control wire 31.

As shown in FIG. 1, the letter A denotes the application side, end or direction referred to herein and the letter C denotes the control side, end or direction as referred to herein. In terms of orienting the ends of the retrieval apparatus 20 and the ends or sides of the component parts and the directions of movement or travel, the conventions of "application side" (A) and "control side" (C) have been adopted and are used herein. As these phrases imply, the application side of either apparatus 20 or of any of the component parts is the side or end which is in the direction or closer to where any treatment, device placement, etc. occurs. Similarly, the control side is the side or end of apparatus 20 or any of the component parts which is in the direction of or closer to where the physician is positioned and denotes where control functions or actions would be performed.

One reason for this adoption is for added clarity since there can be different frames of reference when using "proximal" and "distal". In the medical field "proximal" typically means closer to the heart, but this can change based on the point of entry of a device, such as a catheter, into a patient. Logically, in the medical field, "distal" typically means further from the heart. In other fields, "proximal"

typically means closer to the operator or user and "distal" typically means further from the operator or user. By adopting the conventions of "application side" and "control side", any proximal-distal ambiguity should be eliminated.

Retrieval apparatus 20 is introduced into the IVC 23 by way of wire guide 21 which extends through guide wire cannula 30. Wire guide 21 may remain in position during the retrieval (and removal) procedure described herein or may be removed once the retrieval apparatus is properly positioned as illustrated in FIG. 9. Wire guide 21 is important in the initial introduction of retrieval apparatus 20, but the wire guide 21 is not necessary for proper removal of the retrieval apparatus, with the IVC filter 22 in tow. The advancing and positioning of wire guide 21 is performed using one (1) of the existing technologies or methodologies. Some of the suitable choices for wire guide 21 include a fixed-core wire providing enhanced support, a "nitinol" wire providing shape memory and maneuverability and a hydrophilic wire with a lubricious coating for a low coefficient of friction.

Referring now to FIG. 8, the IVC filter 22 which is to be retrieved and removed is illustrated as positioned in the IVC 23 which is represented by wall 36. In FIG. 9, the IVC filter 22 is illustrated in combination with and in relation to the initial placement of the retrieval apparatus 20 within the IVC 23. This illustrated relationship (see FIG. 9) between retrieval apparatus 20 and IVC filter 22 represents a first step in the retrieval (and ultimately removal) procedure. Actually there are other preliminary steps which have already occurred, but for the retrieval procedure which is illustrated and described herein, the referenced "first" step is to properly position and emplace a suitably-designed retrieval apparatus 20 in proximity to the IVC filter 22 which has been percutaneously placed in the IVC 23. Another "other" step which has already occurred was to actually deliver the IVC filter 22 into the desired position and to ensure that both the positioning and the orientation of the IVC filter 22 are suitable for both capturing emboli and for being retrieved using a removal hook which is provided as a part of the structure of the IVC filter 22.

With continued reference to FIG. 8, IVC filter 22 includes a plurality of spring-biased wire legs or struts 38 and 40 which are constructed and arranged to include a plurality of shorter struts 38 and a plurality of longerstruts 40. The shorter struts 38 are referred to as "secondaries". The longer struts 40 are referred to as "primaries". These two (2) pluralities of struts 38 and 40 are securely anchored together by crimping into the application side end 42 of hub 44. The opposite, control side end 46 of hub 44 includes outwardly extending removal hook 48. Removal hook 48 extends in a control side direction beyond the control side end 46 of hub 44. As illustrated, once IVC filter 22 is deployed, the shorter struts 38 and the longer struts 40 should all be touching the wall 36 of the IVC 23 and collectively spread out across the interior of the IVC 23. As should be understood, IVC filter 22 represents one style of filter which may be employed as part of the disclosed and claimed invention. The described retrieval apparatus (and method) can conceptually be used to retrieve a variety of retrievable filters, including most of those which are currently on the market.

IVC filter 22 was placed in the IVC 23 using a delivery apparatus which introduced (i.e. emplaced) the IVC filter 22 such that the struts were oriented from what was the control side face or end 42 of hub 44. The removal hook 48 extended from what was then viewed as the application side end 46 of hub 44. It is to be noted that various styles of filters which are considered as being retrievable can be alternatively positioned such as in the jugular vein or femoral vein. Whatever the placement, the hook is toward the heart. Stated in another way, the blood flows from the struts toward the hook. In the FIG. 1 illustration for this disclosure, the control side direction is indicated by the letter C and the application side direction is indicated by the letter A, as defined herein. For the retrieval procedure, the point of entry for retrieval apparatus 20 is opposite to the delivery direction. However, the references to control side and application side remain essentially the same, as defined. It is also important for the removal hook 48 and the struts 38 and 40 to be securely connected together, whether by being crimped together into hub 44 or by some other method or structure. At the time of retrieval and removal of IVC filter 22, hook 48 is going to be used for the initial engagement by a loop of the retrieval apparatus 20. Pulling on the hook 48 is part of the removal procedure will exert forces on the hub and in turn will exert forces on the struts 38, 40 tending to want to try and separate either the hook from the hub or the hub from the struts. Staying integrally connected and securely joined is important as part of the retrieval and removal procedure.

Referring now to FIGS. 2 and 2A, outer sheath 24 is an annular, flexible sleeve which is constructed and arranged with a tubular wall 50 defining the hollow interior or lumen 52. Preferably for the intended use as described herein, the length of outer sheath 24 is approximately 65 cm. The gauge of the exemplary embodiment, using the "Fr" scale is approximately 8.5Fr, or approximately 2.83 mm in outside diameter. It is contemplated that a smaller sheath diameter would be acceptable, such as a 7.0Fr size or smaller. Considering the function and use of outer sheath 24, suitable materials for outer sheath 24 include polyethylene and other semi-flexible plastics. These materials represent durable, yet flexible, biocompatible materials which can be readily formed or extruded into the desired starting shape of a generally cylindrical tube or sleeve. The thickness of outer wall 50 depends in part on the select materials, but is generally in the range of 0.008-0.020 inches. Logically, a less durable or less tough material would require a slightly thicker wall.

Since outer sheath 24 represents the radially outermost component, its interior size is selected so as to house the other components, except for dilator 34 and except for the application side end 51 of the wire guide cannula 30. At the same time, the maximum size of the outer tubular wall of sheath 24 must be limited and controlled for placement and travel within the IVC 23. Outer sheath 24 may have a length sufficient to extend outside the patient through a percutaneous entry to the emplacement location for the IVC filter 22. In such embodiments, for instance, a control side portion or end of outer sheath 24, and/or an operating portion attached to it, is outside the body, while an application side portion is adjacent the IVC filter 22 and initially extends over the control side end of IVUS transducer 32. Preferably, outer sheath 24 is of a semi-flexible plastic or other material, such as materials used for intravascular catheters, to allow it to move through vessels while maintaining integrity. Currently available sheaths are sized to be small in diameter while still permitting other components, such as a collapsed filter or snare to fit within them, as is naturally suggested by placement of such sheaths in the vasculature.

The inner sheath 26, referring now to FIGS. 3 and 3A, is an annular, flexible sleeve which is constructed and arranged with a tubular wall 54 defining the hollow inter lumen 56. Preferably, for the intended use as disclosed herein, the length of inner sheath 26 is approximately 75 cm and the outside diameter is approximately 1.2 mm. Considering the function and use of inner sheath 26, suitable materials for the inner sheath 26 include polyethylene and other semi-flexible plastics. These materials each represent durable, yet flexible, biocompatible materials which can be readily formed or extruded into the desired starting shape of a generally cylindrical tube or sleeve. The thickness of outer wall 54 depends in part on the select materials, but is generally in the range of 0.004-0.012 inches. Logically, a less durable or less tough material would require a slightly thicker wall.

The IVUS friendly snare 28, referring now to FIG. 4, is constructed and arranged into four (4) interconnected sections each of which are identified herein as loops 58. These four (4) interconnected loops 58 are each shaped with a tapered end 60 and with an enlarged outer end 62. The generally tear-drop shape of each loop 58 is not substantially planar throughout its entire form. Instead, the outer end (i.e. the larger end) 62 of each loop 58 includes a bend in a radially outwardly direction, as is illustrated. This bending places each outer end 62, at least a portion of each outer end 62, in a generally common geometric plane, i.e. a coplanar arrangement. This coplanar arrangement helps in positioning the outer end 62 of each of the four (4) loops 58 for engaging the removal hook 48 of the IVC filter 22.

The snare 28 is preferably built out of polyimide or alternatively out of stainless steel, using four (4) cannulae 64 for aiding in deployment and structural support of the wire loops 58. Each cannula 64 contains two (2) sections of NiTi which forms each loop 58, extending between adjacent cannula. The sections of cannula are soldered together at a common base or hub 66. The loops 58 are able to be pulled back (i.e. sliding through the corresponding cannulae) so as to close the snare 28 around and onto the removal hook 48. Under IVUS monitoring and guidance, the location of the snare 28 can be determined by looking at the location of the four (4) cannula 64.

The guide wire cannula 30, referring now to FIGS. 5 and 5A, is constructed and arranged with an annular, tubular shape with a sidewall 77 defining a hollow interior 79. The size of hollow interior 79 accommodates receipt of a wire guide in the size range of 0.035-0.040 inches. Although guide wire cannula 30 is described as having a generally tubular shape, guide wire cannula 30 would preferably have a generally cylindrical shape with a substantially uniform sidewall thickness. As such, the overall cannula 30 would have a generally circular shape in lateral section and the hollow interior 79 would preferably have a generally circular shape in lateral section, see FIG. 5A. The guide wire cannula 30 includes an application side end or tip 51, a control side portion 53 and two (2) spaced-apart bends 55 and 57 which define ramp portion 59 therebetween. The application side end 51 is located at the dilator 34 and extends through or passed the IVUS transducer 32. The control side portion 53 represents a section which extends through the interior of retrieval apparatus 20. The two (2) bends 55, 57 create offset ramp portion 59. Ramp portion 59 is positioned adjacent the loops 58 of snare 28 in the initial positioning illustrated in FIG. 9. This offset ramp portion 59 creates a shift in alignment from an edge position to a centered position which is essentially on-axis.

The ultrasound transducer 32, referring now to FIGS. 6 and 6A, is constructed and arranged for use in visualizing the IVC filter 22 and its emplacement, the deployment of snare 28 and the retrieval of IVC filter 22 by engaging a portion of the snare 28 with the removal hook 48. Considering the intravascular positioning and use of ultrasound transducer 32, the acronym IVUS is applicable and is used herein as a shorthand modifier for transducer 32, i.e. IVUS transducer 32. This acronym is also used to reference and describe the manner of guiding and monitoring the retrieval and removal of IVC filter 22. IVUS transducer 32 has a generally cylindrical shape defined by body 65 and its generally cylindrical outer wall 67. Included for alignment and positioning is an application side coaxial hub 32a and a control side coaxial hub 32b. Hub 32a fits within the counterbore in the control side end 74 of dilator 34.

In the exemplary embodiment IVUS transducer 32 includes a stainless steel tubular core 61 surrounded by a ceramic sleeve 63. Wrapped around the ceramic sleeve 63 is a flexible printed circuit board. The IVUS transducer "mechanics" includes an array constructed from a plurality of elements. The array type transducer described above performs scanning by sequentially exciting individual array elements and has no moving parts. Alternate embodiments include a motor driven rotary transducer or a motor driven mirror with a fixed transducer. Due to size considerations, the motor would be external to the patient and would connect to either the element or to the mirror by means of a rotary cable. Alternatively the motor could be micro-sized and incorporated into the application end of the catheter. The central bore 69 is constructed and arranged to receive a portion of guide wire cannula 30 therethrough. The control side end of the IVUS transducer 32 is initially received within the application side end of lumen 52.

The construction represented by the exemplary embodiment of FIGS. 1, 6, 6A and 9 provides a specific arrangement and relationship between the guide wire cannula 30, guide wire 21, IVUS transducer 32 and dilator 34 (i.e. the tip of retrieval apparatus 20). Alternative embodiments are illustrated in FIGS. 14-16 and each of these is described in greater detail hereinafter. Additionally, it is to be noted that the IVUS transducer selection, style, configuration and operation can be varied from what is disclosed for the exemplary embodiment. While one (1) variation is disclosed in FIGS. 14-16, it is further contemplated that a 3D scan capability can be integrated into the selected IVUS transducer. A 3D scan capability could include a single element transducer which is constructed and arranged to be motor driven into two (2) different mechanical axes. Another option for providing this 3D scan capability is to use a linear array transducer and drive it with rotary motion. Another option for providing this 3D scan capability is to use a full 2D linear array. For this option a row-column addressing scheme is used to access different elements for different transmit events.

The dilator 34, referring now to FIGS. 7 and 7A, is constructed and arranged with a generally frustoconical body 70 with a tapering sidewall 72 converging from control side end 74 to application side end 76. Body 70 defines a coaxial central bore 78 which receives an application side end 51 of guide wire cannula 30. Counterbore 78a is coaxial with bore 78 and is sized and shaped to receive an application side hub 32a of IVUS transducer 32. Guide wire cannula 30 in cooperation with wire guide 21 are used and assists in positioning the retrieval apparatus 20 for IVC filter 22 retrieval and is used to assist in removing the IVC filter 22 from the patient. Wire guide 21 is not required for the removal steps. In order to properly perform these integrated functions, the application side end 51 of guide wire cannula 30 is securely anchored within central bore 78. This secure relationship preferably includes compatible sizes and shapes for the central bore 78 and the application side end 51. Dilator 34 is located at the application side end of the retrieval apparatus 20 and receives the application side end of guide wire cannula 30.

Referring now to FIGS. 9-13, and with continued reference to FIGS. 1 and 8, these drawings figures depict the structural configurations associated with the steps or stages in the retrieval of an emplaced IVC filter 22 and removal of that IVC filter 22 from a patient. The first step of the retrieval method, following entry of the retrieval apparatus 20 into the vein, is to establish the proper positioning of the retrieval apparatus 20 relative to the location of the IVC filter 22. The proper initial positioning of retrieval apparatus 20 is illustrated in FIG. 9. A key aspect of this first step of the retrieval procedure or method is to position the retrieval apparatus 20 such that the imaging plane 84 of the IVUS transducer 32 coincides with the location of the removal hook 48 of the IVC filter 22. This geometric plane of coincidence is illustrated by broken line 84. As would be understood, the drawing figures are diagrammatic and are not necessarily drawn to scale. As illustrated, the initially withdrawn and collapsed loops 58 of snare 28 are captured by the outer sheath 24. The spring-biased quality of the loops 58 and the wire used for the loops in part makes this capture possible. These characteristics enable the snare 28 to open when the capturing outer sheath is pulled back and the wires extended to open the loops 58, a maneuver which is part of the next step in the overall method.

The next step in the method of IVC filter 22 retrieval and ultimately removal from the vein, is illustrated in FIG. 10. In this step, the outer sheath 24 is pulled back slightly in a control side direction. This action creates an opening 92. The removal of the restraining outer sheath 24 allows the loops 58 of the snare 28 to open up from their captured and collapsed condition. The wires which comprise the loops 58 are captured by the cannulae 64 and able to slide therethrough. This allows the closed loops to be enlarged as they open and extend or travel outwardly and toward the application side direction through opening 92. Then, after this step is performed, the "IVUS friendly" snare 28 is advanced, in an application side direction, into alignment with the removal hook 48. The intent is to be able to "hook" or secure one of the loops 58 of the snare 28 onto the removal hook 48 of the IVC filter 22. One of the techniques to improve the probability of one of the loops 58 of the snare 28 engaging the hook 48 is to have the outer end 62 of each loop 58 bent into a generally planar configuration such that the upper end 62 of each loop 58 is similarly bent over such that all bent portions 62 are generally coplanar with one another. The geometric plane which includes these bent portions of the outer end 62 of each loop 58 is generally coincident with the geometric plane which includes the curved portion of removal hook 48. Alignment can be confirmed by imaging using the IVUS transducer 32.

If it appears from IVUS imaging visualization that there is a suitable relationship between the loops 58 and the removal hook 48, the method of retrieval continues. The next step in the method of retrieval (and removal) is to advance the inner sheath 26 in an application side direction. This step is illustrated in FIG. 11. The inner sheath 26 is able to be moved independently of the snare 28 and independently of the outer sheath 24. The tapered design of the individual loops 58 and their common connection to the application side face of the hub enables the application side, open end of the inner sheath to be able to readily slide over the hub and over the starting portion (i.e. base) of the joined loops 58. Once the hub and the ends of the individual loops are received within the open end of the inner sheath 26, the inner sheath 26 can be easily advanced into the position illustrated in FIG. 11. The wires comprising the loops 58 can be withdrawn somewhat concurrently so as to reduce the size of each loop being collapsed.

The advancing inner sheath 26 closes the loops 58 into a tighter nest and in so doing, the loops 58 close securely around the removal hook 48. The IVUS transducer 32 is used for imaging the movement of these components as part of the method steps. The IVUS transducer 32 is used for monitoring the relationship between the loops 58 and the removal hook 48 to ensure that the snare 28 properly engages the removal hook 48 for retrieval and removal the IVC filter 22.

The next step in the described method is to advance the retrieval apparatus 20 approximately 5.5 cm in the application side direction, as illustrated in FIG. 12. This distance is measured using sheath markers (not illustrated). In the next step, as illustrated in FIG. 13, the outer sheath 24 is advanced in an application side direction. This action of the outer sheath 24 causes the outwardly-extending struts 38 and 40 to be engaged and to being to collapse inwardly. The force exerted by the action of the outer sheath 24 on the struts 38 and 40 initiate separation of the struts from the wall of the vein. With continued advancing, see FIG. 13, the IVC filter 22 is captured within retrieval apparatus 20. Once the outer sheath 24 is advanced into the concluding position over IVUS transducer 32, the retrieval apparatus 20, now with the captured IVC filter 22, is ready to be removed from the vein of the patient.

The use of IVUS transducer 32 enables the IVC filter 22 to be retrieved under ultrasound guidance, an improvement to the use of a percutaneous retrieval set and fluoroscopy suite as representative of the prior art. The retrieval snare 28 is constructed and arranged so that it can be easily seen and located under IVUS guidance. The retrieval apparatus 20 is constructed and arranged to include an IVUS transducer 32 built into the apparatus 20 adjacent a control side end of the dilator 34. Guide wire cannula 30 extends through the IVUS transducer 32 and the end of guide wire cannula 30 is received within dilator 34. This construction enables the IVC filter 22 retrieval and removal method to be performed through a single access point, without a need for an exchange of catheters. The retrieval apparatus is constructed and arranged in order to maintain important snare 28 and IVC filter 22 features in the imaging plane of the IVUS transducer 32 during retrieval of the IVC filter 22.

Retrieval apparatus 20 allows IVC filter 22 retrieval to be easily performed under ultrasound guidance. In order to facilitate this aspect, the snare 28 is constructed and arranged so that its positioning is easily ascertainable under ultrasound guidance. The IVUS transducer is located so that its imaging plane captures relevant information, such as the position of the IVC filter 22 and the location of snare 28 during the retrieval steps of the disclosed method. As noted, all of this is accomplished through a single access site, without the need for an exchange of catheters.

Referring now to FIGS. 14-16, three (3) other embodiments for the application side end of a retrieval apparatus are illustrated. Referring first to FIG. 14, an IVUS filter retrieval apparatus 100 is disclosed which includes an embedded IVUS transducer 102. This embodiment offers design options for the IVUS transducer 102, the "rapid exchange" wire guide 104 and the tip 106. This embodiment is not dependent on the specific configuration of the IVUS transducer 102.

Optionally, the IVUS transducer may be hollow or may not be hollow, the latter being disclosed as IVUS transducer 102. As such, the alternatives which are available and compatible with the illustrated structure of retrieval apparatus 100 include, as one (1) option, the use of a torque cable driven transducer. Other options include the use of an on-site motor rotary transducer, array transducers and 3D transducers in a variety of configurations.

The retrieval apparatus includes a snare 28 and a mechanical support 108 which provides a connection between the application side or end of the catheter 110 where the tip 106 and transducer 102 are positioned and the control side or end where the snare 28 and the main body of the catheter 110 are positioned.

In the exemplary embodiment of FIG. 14, the mechanical support 108 is hollow and is constructed and arranged to be able to receive a wire guide, transducer cabling, a torque cable, a fluid lumen, etc. Alternatively, the mechanical support may be a solid member. The application side or end, denoted by the letter A, includes the tip 106 which is adjacent one (1) end of the transducer 102.

As illustrated in FIGS. 14, 15 and 16, several design options are available for the transducer tip 106. One (1) option associated with the FIG. 14, is to configure the transducer tip 106 with a rapid-exchange lumen 112. Another option, associated with FIG. 15, is to configure the wire guide 114 and transducer tip 116 such that one (1) end of the wire guide 114 is permanently embedded into a receiving aperture 118 in the application side or end of the transducer tip 116. Another option, associated with FIG. 16, is to eliminate the wire guide (104, 114) and instead round or contour the application side or end of tip 120 with a substantially hemispherical shape. This substantially hemispherical shape at the leading edge or face reduces the risk of puncture or tearing of a vessel as the corresponding retrieval apparatus is moved into the desired position.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A retrieval apparatus for removing an intravascular filter from a body vessel of a patient, said retrieval apparatus comprising:
an outer sheath having an annular wall defining an outer lumen;
an inner sheath having an annular wall defining an inner lumen, said inner sheath being positioned in said outer lumen and being constructed and arranged for use in removing said intravascular filter from said body vessel;
a retrieval member positioned in said inner lumen, said retrieval member including a snare with a plurality of loops;
an ultrasound transducer positioned on an application side of said retrieval member, said inner sheath being adapted to move independently of said ultrasound transducer;
a guide wire cannula extending between said outer sheath and said inner sheath; and
a dilator located on the application side of said retrieval member, said dilator being coupled to said ultrasound transducer and receiving said guide wire cannula, wherein said plurality of loops are used for aligning with said intravascular filter such that extending said inner sheath toward said plurality of loops closes said snare toward a portion of said intravascular filter.

2. The retrieval apparatus of claim 1 wherein said retrieval member includes a plurality of cannulae and a plurality of loop wires forming said plurality of loops wherein each loop wire has one portion extending through one cannula and another portion extending through an adjacent cannula.

3. The retrieval apparatus of claim 2 wherein an upper portion of each loop is bent over into a coplanar arrangement.

4. The retrieval apparatus of claim 2 wherein said plurality of loops includes four loops which are interconnected.

5. The retrieval apparatus of any of claim 2 wherein said plurality of cannulae are joined to a common hub.

6. The retrieval apparatus of claim 2 wherein an upper portion of each loop of said plurality of loops is adjacent a ramp portion of said guide wire cannula.

7. The retrieval apparatus of any of claim 1 wherein said retrieval member includes a plurality of interconnected cannulae.

8. The retrieval apparatus of claim 1 wherein a control side portion of said ultrasound transducer is received within said outer lumen.

9. The retrieval apparatus of claim 1 wherein said guide wire cannula includes an application side portion, a control side portion and a ramp portion which is located between said application side portion and said control side portion.

10. The retrieval apparatus of claim 1 wherein said outer sheath is constructed and arranged to be movable in a control side direction independently of said ultrasound transducer.

11. The retrieval apparatus of claim 1 wherein said retrieval member is constructed and arranged to be movable in an application side direction independently of said ultrasound transducer.

12. The retrieval apparatus of claim 1 wherein said outer sheath and said inner sheath are each cooperatively constructed and arranged such that one sheath is movable independently of the other sheath.

13. A retrieval apparatus for retrieving an inferior vena cava (IVC) filter from an IVC of a patient, said retrieval apparatus comprising:
an outer sheath having an annular wall defining an outer lumen;
an inner sheath having an annular wall defining an inner lumen, said inner sheath being positioned in said outer lumen and being constructed and arranged for use in removing said IVC filter from said IVC;
a retrieval member positioned in said inner lumen, said retrieval member including a snare with a plurality of loops;
an intravascular ultrasound (IVUS) transducer positioned on an application side of said retrieval member, said inner sheath being adapted to move independently of said IVUS transducer;
a guide wire cannula extending between said outer sheath and said inner sheath, said guide wire cannula including an application side end; and
a dilator located at an application side end of said retrieval apparatus, said dilator being coupled to said IVUS transducer and receiving the application side end of said guide wire cannula, wherein said plurality of loops are used for aligning with said IVC filter such that extending said inner sheath toward said plurality of loops closes said snare toward a portion of said IVC filter.

14. The retrieval apparatus of claim 13 wherein said retrieval member includes a plurality of cannulae and a plurality of loop wires forming said plurality of loops wherein each loop wire has one portion extending through one cannula and another portion extending through an adjacent cannula.

15. The retrieval apparatus of claim 14 wherein an upper portion of each loop is bent over into a coplanar arrangement.

16. The retrieval apparatus of claim 14 wherein the plurality of loops includes four loops which are interconnected.

17. The retrieval apparatus of claim 13 wherein said retrieval member includes a plurality of interconnected cannulae.

18. The retrieval apparatus of claim 13 wherein said IVUS transducer is positioned adjacent a control side counterbore of said dilator.

19. The retrieval apparatus of claim 18 wherein said guide wire cannula extends through said IVUS transducer.

20. The retrieval apparatus of claim 19 wherein said application side end of said guide wire cannula is received within said dilator.

21. A method of retrieving an intravascular filter from a body vessel of a patient using a retrieval apparatus which includes an outer sheath, an inner sheath, a retrieval member including a snare with a plurality of loops and a delivery device, an ultrasound transducer, a guide wire cannula and a dilator, wherein said ultrasound transducer comprises an imaging plane, said method comprising the following steps:
providing said retrieval apparatus;
inserting said retrieval apparatus into the body vessel of the patient;
positioning said retrieval apparatus such that said imaging plane coincides with a selected location within the patient;
manipulating said retrieval apparatus so as to move said retrieval member independently of said ultrasound transducer toward said imaging plane;
positioning a portion of said snare into said imaging plane by retracting said outer sheath to create an opening for said plurality of loops to open outwardly and deploy;
aligning said plurality of loops with said intravascular filter;
closing said snare onto a portion of said intravascular filter by extending said inner sheath toward said plurality of loops;
retracting said inner sheath and said snare with said intravascular filter, into said outer sheath; and withdrawing said retrieval apparatus with said intravascular filter.

22. The method of claim 21 wherein said intravascular filter includes a removal hook, wherein said step of positioning a portion of said snare includes positioning said portion of said snare adjacent said removal hook.

23. The method of claim 22 wherein said portion of said intravascular filter includes said removal hook.

24. A retrieval apparatus for removing an intravascular filter from a body vessel of a patient, said retrieval apparatus comprising:
an outer sheath having an annular wall defining an outer lumen;
an inner sheath having an annular wall defining an inner lumen, said inner sheath being positioned in said outer lumen and being constructed and arranged for use in removing said intravascular filter from said body vessel;
a retrieval member positioned in said inner lumen, said retrieval member including a snare with a plurality of loops;
an ultrasound transducer positioned on an application side of said retrieval member, said inner sheath being adapted to move independently of said ultrasound transducer; and
a guide wire cannula extending between said outer sheath and said inner sheath, said ultrasound transducer receiving said guide wire cannula, wherein said plurality of loops are used for aligning with said intravascular filter such that extending said inner sheath toward said plurality of loops closes said snare toward a portion of said intravascular filter.

25. A retrieval apparatus for retrieving an inferior vena cava (IVC) filter from an IVC of a patient, said retrieval apparatus comprising:
an outer sheath having an annular wall defining an outer lumen;
an inner sheath having an annular wall defining an inner lumen, said inner sheath being positioned in said outer lumen and being constructed and arranged for use in removing said IVC filter from said IVC;
a retrieval member positioned in said inner lumen, said retrieval member including a snare with a plurality of loops;
an intravascular ultrasound (IVUS) transducer positioned on an application side of said retrieval member, said inner sheath being adapted to move independently of said IVUS transducer; and
a guide wire cannula extending between said outer sheath and said inner sheath, said guide wire cannula including an application side end and receiving said IVUS transducer, wherein said plurality of loops are used for aligning with said IVC filter such that extending said inner sheath toward said plurality of loops closes said snare toward a portion of said IVC filter.

26. The retrieval apparatus of claim 1 wherein said ultrasound transducer is positioned adjacent a control side counterbore of said dilator.

27. The retrieval apparatus of claim 26 wherein said guide wire cannula extends through said ultrasound transducer.

28. The retrieval apparatus of claim 27 wherein said guide wire cannula has an application side end which is received within said dilator.

* * * * *